United States Patent
Hara et al.

(10) Patent No.: US 12,290,336 B2
(45) Date of Patent: May 6, 2025

(54) PATHOGEN DETECTION APPARATUS AND PATHOGEN DETECTION METHOD

(71) Applicant: Panasonic Intellectual Property Management Co., Ltd., Osaka (JP)

(72) Inventors: Kohei Hara, Osaka (JP); Kazuaki Nishio, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 851 days.

(21) Appl. No.: 17/315,419

(22) Filed: May 10, 2021

(65) Prior Publication Data

US 2021/0259556 A1   Aug. 26, 2021

Related U.S. Application Data

(63) Continuation of application No. PCT/JP2020/003633, filed on Jan. 31, 2020.

(30) Foreign Application Priority Data

Mar. 6, 2019 (JP) .................. 2019-041038

(51) Int. Cl.
  *A61B 5/01*    (2006.01)
  *A61B 5/00*    (2006.01)
  (Continued)

(52) U.S. Cl.
  CPC .............. *A61B 5/01* (2013.01); *A61B 5/082* (2013.01); *A61B 5/097* (2013.01); *A61B 5/74* (2013.01); *A61B 5/0059* (2013.01); *G01N 1/2211* (2013.01)

(58) Field of Classification Search
  CPC ........... A61B 5/01; A61B 5/082; A61B 5/097; A61B 5/74; A61B 5/0059; G01N 1/2211
  See application file for complete search history.

(56) References Cited

U.S. PATENT DOCUMENTS

2010/0015601 A1* 1/2010 Gilmore ............... G01N 1/2202
                                                        506/7
2014/0323819 A1* 10/2014 Hyde ................. A61B 10/0051
                                                        600/301
(Continued)

FOREIGN PATENT DOCUMENTS

JP       2008-070321       3/2008
JP       2015-178993       10/2015
(Continued)

OTHER PUBLICATIONS

International Search Report of PCT application No. PCT/JP2020/003633 dated Mar. 24, 2020.
(Continued)

*Primary Examiner* — Eric J Messersmith
*Assistant Examiner* — Kyle W. Kretzer
(74) *Attorney, Agent, or Firm* — Wenderoth, Lind & Ponack L.L.P.

(57) ABSTRACT

A pathogen detection apparatus includes an obtainer that measures a body temperature of a subject and outputs information indicating the body temperature, a collector that performs a pathogen collection operation for collecting a pathogen carried by the subject or a pathogen in air around the subject, a detector that performs a pathogen detection operation for detecting the pathogen collected by the collector, a notifier that provides a notification indicating a detection result obtained by the detector, and a controller. In a case where the body temperature output by the obtainer is higher than a predetermined threshold value and the detection result obtained by the detector is negative, the controller controls the detector to perform another pathogen detection operation for detecting a pathogen.

9 Claims, 8 Drawing Sheets

(51) Int. Cl.
  *A61B 5/08*    (2006.01)
  *A61B 5/097*   (2006.01)
  *G01N 1/22*    (2006.01)

(56) References Cited

U.S. PATENT DOCUMENTS

2017/0119280 A1* 5/2017 Ahmad ................. A61B 5/097
2020/0333338 A1  10/2020 Kori et al.
2021/0007627 A1* 1/2021 Koehl ................. G01N 33/497

FOREIGN PATENT DOCUMENTS

JP  2015-206670       11/2015
JP  2015206670 A  *  11/2015
WO  2019/193878      10/2019

OTHER PUBLICATIONS

Lincoln L. H. Lau et al., "Viral Shedding and Clinical Illness in Naturally Acquired Influenza Virus Infections", The Journal of Infectious Diseases, 2010, vol. 201, No. 10, Apr. 12, 2010, pp. 1509-1516.
English Translation of Search Report issued Dec. 18, 2023 in corresponding Chinese Patent Application No. 202080006060.8.

* cited by examiner

PATHOGEN DETECTION APPARATUS AND PATHOGEN DETECTION METHOD

BACKGROUND

1. Technical Field

The present disclosure relates to a pathogen detection apparatus and a pathogen detection method that change a pathogen detection operation in accordance with a subject.

2. Description of the Related Art

The spread of infectious diseases, such as influenza, in nursing homes, hospitals, schools, and the like is a social issue. Japanese Unexamined Patent Application Publication No. 2015-178993 discloses measuring of the concentration of a virus suspended in the air using fluorescence spectroscopy, surface-enhanced Raman scattering spectroscopy, or an immunochromatographic device using an antigen-antibody reaction.

The following literature discloses that the quantity of virus carried by an infected person is correlated with his/her body temperature and that the body temperature is proportional to the quantity of virus: Lincoln L. H. Lau, Benjamin J. Cowling, Vicky J. Fang, Kwok-Hung Chan, Eric H. Y. Lau, Marc Lipsitch, Calvin K. Y. Cheng, Peter M. Houck, Timothy M. Uyeki, J. S. Malik Peiris, and Gabriel M. Leung, "Viral Shedding and Clinical Illness in Naturally Acquired Influenza Virus Infections", The Journal of Infectious Diseases, 201 1509-1516 (2010).

SUMMARY

In the related art, a positive or negative determination is made on the basis of whether or not a pathogen has been detected, regardless of the condition of a subject. This may cause a false negative resulting from a sampling error or the like in the case of, for example, collecting and detecting a pathogen contained in breath of the subject.

One non-limiting and exemplary embodiment provides a technique capable of reducing false negatives in pathogen detection from subjects.

In one general aspect, the techniques disclosed here feature a pathogen detection apparatus including an obtainer that measures a body temperature of a subject and outputs information indicating the body temperature, a collector that performs a pathogen collection operation for collecting a pathogen carried by the subject or a pathogen in air around the subject, a detector that performs a pathogen detection operation for detecting the pathogen collected by the collector, a notifier that provides a notification indicating a detection result obtained by the detector, and a controller. In a case where the body temperature output by the obtainer is higher than a predetermined threshold value and the detection result obtained by the detector is negative, the controller controls the detector to perform another pathogen detection operation for detecting a pathogen.

It should be noted that general or specific embodiments may be implemented as a method, a system, an integrated circuit, a computer program, or a computer-readable recording medium, or may be implemented as any selective combination of an apparatus, a system, a method, an integrated circuit, a computer program, and a computer-readable recording medium. The computer-readable recording medium includes, for example, a nonvolatile recording medium, such as a compact disc-read only memory (CD-ROM).

According to the present disclosure, false negatives in pathogen detection from subjects can be reduced. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Hereinafter, an embodiment of the present disclosure will be described with reference to the drawings.

Embodiment

Overview of Pathogen Detection Apparatus

A pathogen detection apparatus has a collection function capable of colleting pathogens including viruses suspended in the air, such as an influenza virus, and a function of detecting a pathogen by testing an extraction liquid containing the collected pathogens. The detection is performed by using antibodies that bind specifically to pathogen components contained in the extraction liquid containing the pathogens, with use of a function in which antibodies bind specifically to antigens.

Figure 1:
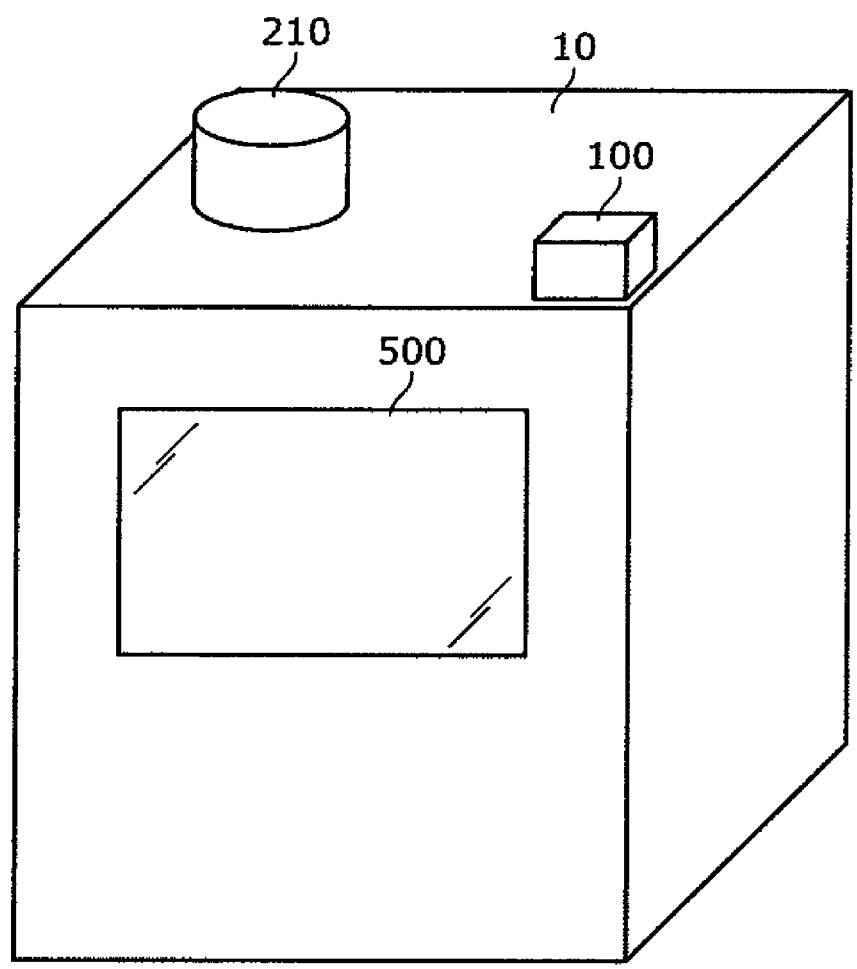
FIG. 1 is a diagram illustrating an example of the external appearance of a pathogen detection apparatus according to an embodiment.

FIG. 1 is a diagram illustrating an example of the external appearance of a pathogen detection apparatus 10 according to an embodiment.

The pathogen detection apparatus 10 is configured to collect breath exhaled by a subject (for example, a subject who undergoes a test for determining whether he/she has a pathogen, performed by the pathogen detection apparatus 10) directly from the subject. The pathogen detection apparatus 10 includes, as illustrated in FIG. 1, for example, a body temperature measurement device 100 that measures a body temperature of a person, an air intake port 210 for collecting air as a detection target, and a display device 500 that displays a detection result, which are exposed on the outer side of a housing. The external appearance of the pathogen detection apparatus 10 illustrated in FIG. 1 is an example, and is not limited to this configuration.

Figure 2:
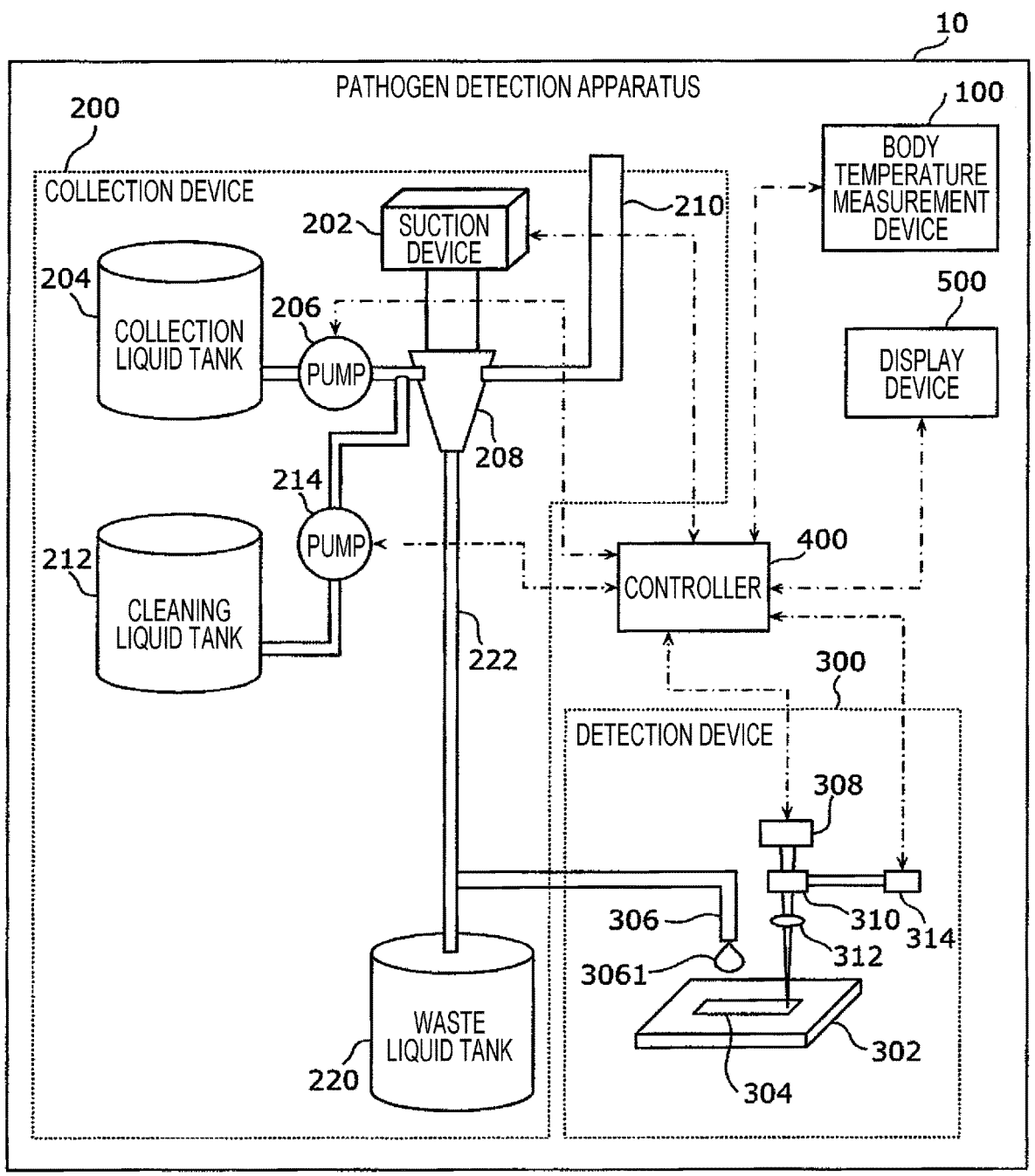
FIG. 2 is a diagram illustrating a schematic configuration of the pathogen detection apparatus according to the embodiment.

FIG. 2 is a diagram illustrating a schematic configuration of the pathogen detection apparatus 10 according to the embodiment.

As illustrated in FIG. 2, the pathogen detection apparatus 10 includes the body temperature measurement device 100, a collection device 200, a detection device 300, a controller 400, and the display device 500. Hereinafter, the details of the body temperature measurement device 100, the collection device 200, the detection device 300, the controller 400, and the display device 500 will be described.

Body Temperature Measurement Device

The body temperature measurement device 100 is a temperature sensor that measures a body temperature of a subject. The body temperature measurement device 100 is, for example, a contact temperature sensor that measures a body temperature of a subject by touching the body of the subject or a non-contact temperature sensor that measures a body temperature of a subject without touching the body of the subject. The contact temperature sensor is, for example, a temperature sensor using a thermocouple or the like. The non-contact temperature sensor is, for example, a temperature sensor that measures a body temperature by measuring the quantity of infrared radiation from the body of a subject by using an infrared sensor. The body temperature measurement device 100 is not limited to the above-described examples, and another existing device capable of measuring a body temperature of a subject may be used. The body temperature measurement device 100 may include a memory that stores a body temperature measurement result.

The body temperature measurement device 100 may store, in the memory, as a body temperature measurement result, the date and time of measurement of a body temperature and/or identification information identifying a subject having the body temperature in association with the measured body temperature. The body temperature measurement device 100 outputs the body temperature measurement result to the controller 400.

Configuration of Collection Device

The collection device 200 collects microparticles that may contain pathogens in the air and mixes the microparticles into a collection liquid. As illustrated in FIG. 2, the collection device 200 includes a suction device 202, a collection liquid tank 204, a pump 206, a cyclone 208, the air intake port 210, a cleaning liquid tank 212, a pump 214, a waste liquid tank 220, and a liquid channel 222. Hereinafter, the individual elements of the collection device 200 will be described.

The suction device 202 sucks in surrounding atmospheric air through the air intake port 210. The surrounding atmospheric air contains microparticles suspended therein. The microparticles may contain pathogens. The surrounding atmospheric air is sucked into the cyclone 208 through the air intake port 210.

The collection liquid tank 204 is a container for holding a collection liquid for collecting pathogens in the air.

The pump 206 supplies the cyclone 208 with the collection liquid in the collection liquid tank 204.

The cyclone 208 is connected to the air intake port 210 and the collection liquid tank 204, and mixes the microparticles that may contain pathogens in the air sucked by the suction device 202 through the air intake port 210 and the collection liquid supplied from the collection liquid tank 204 by the pump 206. The cyclone 208 is connected to the detection device 300 via the liquid channel 222. The collection liquid mixed with the microparticles (hereinafter referred to as a specimen) is discharged from the cyclone 208 to the detection device 300 via the liquid channel 222.

The cleaning liquid tank 212 is a container for holding a cleaning liquid for cleaning the cyclone 208 and the liquid channel 222. The cleaning liquid tank 212 is connected to the cyclone 208, and the cleaning liquid in the cleaning liquid tank 212 is supplied to the cyclone 208 by the pump 214.

The waste liquid tank 220 is a container for storing an unnecessary liquid.

The liquid channel 222 is a path for leading a specimen discharged from the cyclone 208 to the detection device 300.

Figure 3:
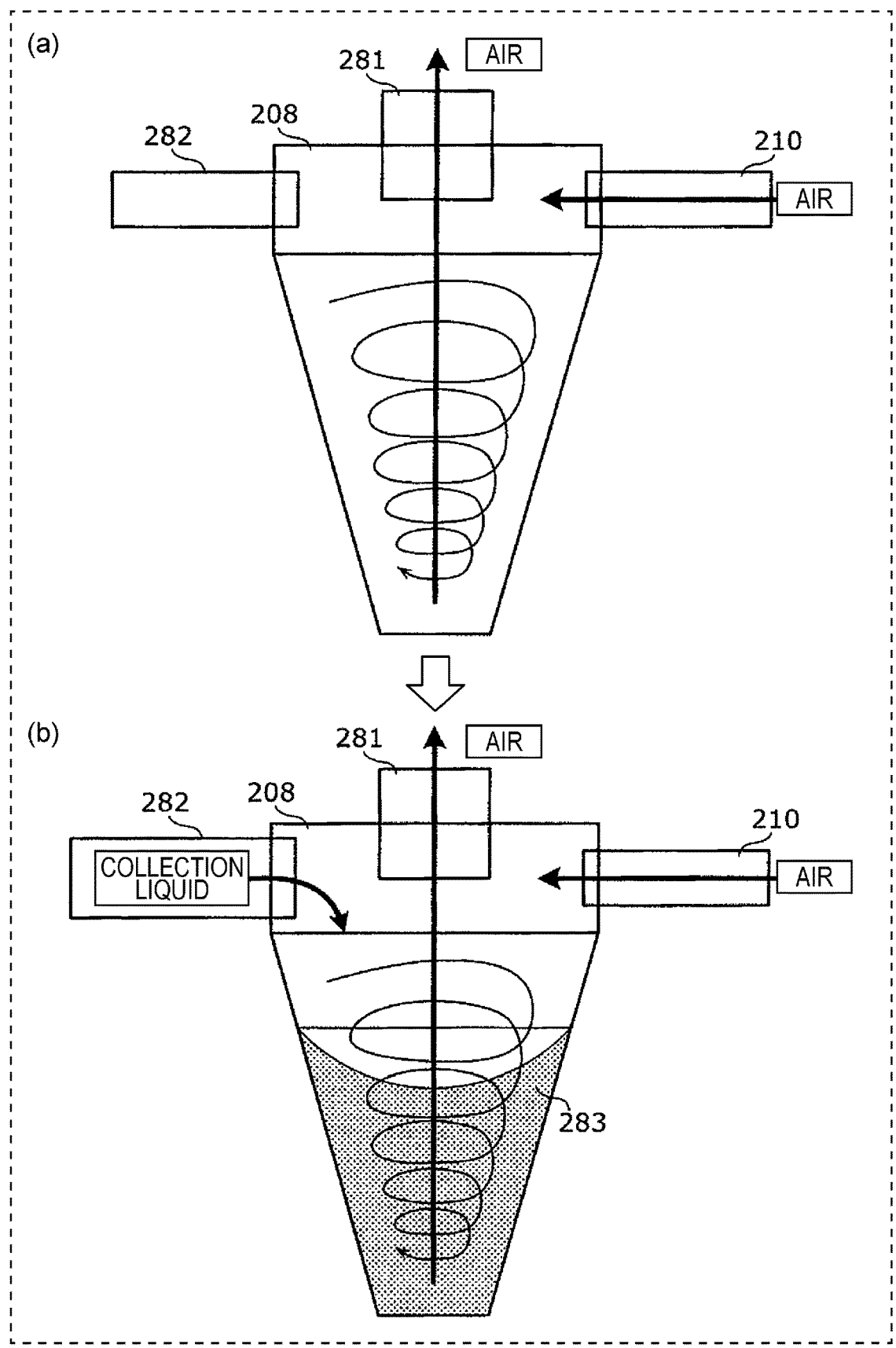
FIG. 3 is a diagram for describing the function of a cyclone according to the embodiment.

FIG. 3 is a diagram for describing the function of the cyclone 208 according to the embodiment.

To collect viruses suspended in the air, such as an influenza virus, it is necessary to take in a large quantity of air and collect viruses in the taken air into a liquid because it is estimated that only a very small quantity of virus is suspended in the air. Here, the viruses are collected into the liquid to typically perform the above-mentioned binding between antibodies and virus components in a solution. The liquid may be pure water from which impurities have been removed, or a solution prepared by dissolving in pure water a phosphate buffer typically used as a solvent of a biological material, so as not to denature the virus components. For example, phosphate buffered saline (PBS), Tris, and the like are available.

The cyclone 208 may be used to take in a large quantity of air. In the cyclone 208, as illustrated in FIG. 3(a), air is sucked through a suction port 281 connected to the suction device 202, and thereby the air is taken into the cyclone 208 through the air intake port 210. The taken air is rotated at a high speed in the cyclone 208. At this time, microparticles contained in the taken air and having a size larger than or equal to a certain size are unable to follow an air flow in the cyclone 208 and are centrifugally blown toward an inner wall surface of the cyclone 208, thereby being separated from the air. The microparticles separated from the air are collected at a lower portion of the cyclone 208.

In this way, the suction into the cyclone 208 causes an influenza virus suspended in the air to enter the cyclone 208 through the air intake port 210 and to be centrifugally blown toward the inner wall surface of the cyclone 208. In a case where the lower portion of the cyclone 208 is filled with a predetermined quantity of collection liquid 283 before starting of the suction, an airflow in the cyclone 208 causes the collection liquid 283 to spirally rotate and to rise along the inner wall surface of the cyclone 208 as illustrated in FIG. 3(b), and an influenza virus blown toward the inner wall surface can be captured in the solution. The collection liquid 283 is supplied, for example, from a collection liquid intake port 282 of the cyclone 208 connected to the pump 206 into the cyclone 208.

The collection device 200 may collect viruses from a mucous membrane or mucus of a subject collected from the pharynx, nasal cavity, or the like of the subject by using a specimen collecting tool, such as a sterilized swab, or may collect viruses from mucus or the like collected by nasal aspiration, instead of collecting viruses from the air. Collecting of viruses by the collection device 200 is not limited to the above-described examples, and another existing method may be used as long as a virus can be collected from a subject.

Configuration of Detection Device

Figure 4:
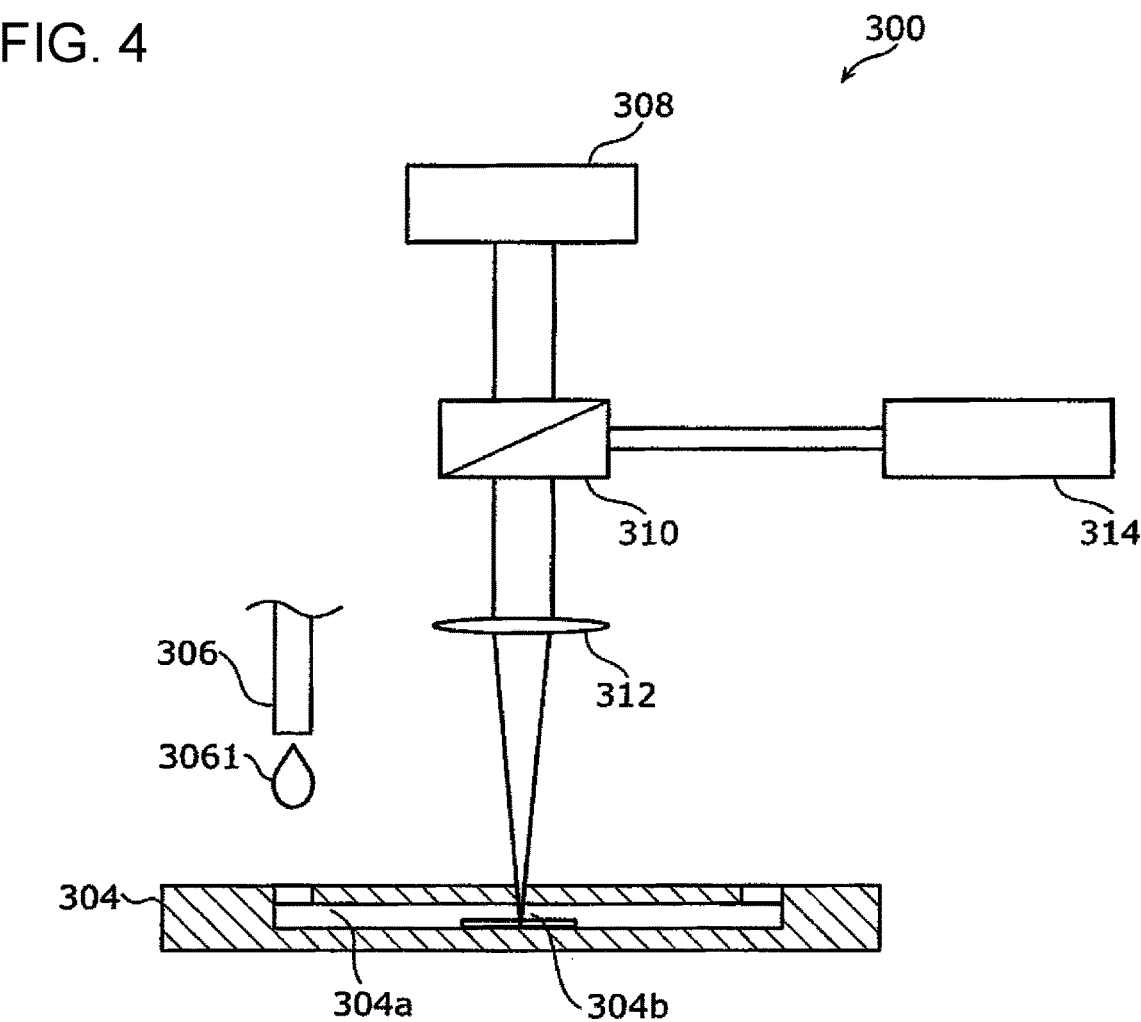
FIG. 4 is a diagram illustrating the configuration of a detection device according to the embodiment.

The detection device 300 will be described in detail with reference to FIG. 2 and FIG. 4. FIG. 4 is a diagram illustrating the configuration of the detection device 300 according to the embodiment.

The detection device 300 detects the quantity of virus from a collection liquid mixed with microparticles by the collection device 200. As illustrated in FIG. 2 and FIG. 4, the detection device 300 includes a sensor device 302, a loading unit 306, a light source 308, a beam splitter 310, a lens 312, and a detection unit 314. Hereinafter, the individual elements of the detection device 300 will be described.

The sensor device 302 includes a sensor cell 304. In FIG. 2, the sensor device 302 includes the single sensor cell 304. Alternatively, the sensor device 302 may include sensor cells.

In the present embodiment, the sensor device 302 is capable of detecting a virus in a concentration range from 0.1 pM to 100 nM. In the present embodiment, a surface-enhanced fluorescence method is used to optically detect the quantity of virus.

The sensor cell 304 generates surface plasmons when irradiated with excitation light, thereby enhancing fluorescence emitted by a fluorescent substance bound to a virus. As illustrated in FIG. 4, the sensor cell 304 includes a channel 304a and a detection region 304b.

The channel 304a is a path for leading a sample liquid 3061 dropped by the loading unit 306 to the detection region 304b.

The detection region 304b is a region for optically detecting a virus by using surface plasmons. A metal microstructure as illustrated in FIG. 6, for example, is disposed in the detection region 304b, where surface plasmons are generated upon irradiation with excitation light from the light source 308. First antibodies are immobilized on the metal microstructure. The first antibodies are immobilized antibodies that bind specifically to a virus. The details of the detection region 304b will be described below with reference to FIG. 4 and FIG. 5.

The loading unit 306 loads second antibodies and a specimen to the sensor cell 304. Specifically, the loading unit 306 drops the sample liquid 3061 containing the second antibodies and the specimen onto the sensor cell 304. The second antibodies are labeled antibodies labeled with fluorescent substances. The specimen is a liquid that may contain a virus and is, in the present embodiment, a collection liquid discharged by the cyclone 208.

If the specimen contains a virus, the virus binds to the metal microstructure via the first antibodies. At this time, the virus also binds to the second antibodies labeled with fluorescent substances. In other words, complexes each made up of a first antibody, a virus, a second antibody, and a fluorescent substance bind to the metal microstructure. When the metal microstructure is irradiated with light in this state, the fluorescent substances indirectly bound to the virus emit fluorescence, and the fluorescence is enhanced by surface plasmons. Hereinafter, the fluorescence enhanced by surface plasmons will be referred to as surface-enhanced fluorescence.

The light source 308 is an example of a light irradiator that irradiates the sensor cell 304 with excitation light. Any existing technique can be used as the light source 308 without particular limitation. For example, a laser such as a semiconductor laser or a gas laser can be used as the light source 308. The light source 308 may radiate excitation light whose wavelength has a small interaction with a substance contained in a virus (for example, 400 nm to 2000 nm). Furthermore, the wavelength of the excitation light may be 600 nm to 850 nm that can be used by a semiconductor laser.

The beam splitter 310 separates the surface-enhanced fluorescence generated in the detection region 304b from the excitation light radiated by the light source 308. Specifically, the beam splitter 310 allows the excitation light from the light source 308 to pass therethrough, separates the surface-enhanced fluorescence generated in the sensor cell 304 from the excitation light, and leads the surface-enhanced fluorescence to the detection unit 314.

The lens 312 condenses the excitation light radiated by the light source 308 and passed through the beam splitter 310 onto the detection region 304b.

The detection unit 314 divides the surface-enhanced fluorescence led by the beam splitter 310 and detects light in a specific wavelength range, thereby outputting an electric signal corresponding to the quantity of virus in the specimen. Any existing technique capable of detecting light in the specific wavelength range can be used as the detection unit 314 without particular limitation. For example, an interference filter that allows a specific wavelength range to pass therethrough to divide light, a Czerny spectrometer that divides light by using a diffraction grating, an Echelle spectrometer, or the like can be used as the detection unit 314. Furthermore, the detection unit 314 may include a notch filter for removing the excitation light from the light source 308, or a long-pass filter that is capable of blocking the excitation light from the light source 308 and allowing the surface-enhanced fluorescence generated by the sensor cell 304 to pass therethrough.

In a case where the detection unit 314 performs detection of a virus concentration with high accuracy when a virus concentration is low, the time taken to complete the detection is long. In other words, the accuracy of measuring a virus concentration can be increased by increasing the time taken for detection (the details will be described below).

The detection device 300 may include a memory storing correlation data between intensities of light in a specific wavelength range and virus concentrations. In a case where the detection unit 314 detects an intensity of light in the specific wavelength range, the detection unit 314 may specify the virus concentration corresponding to the detected intensity in the correlation data stored in the memory, and may output the specified virus concentration as the virus concentration detected by the detection unit 314.

In the case of generating correlation data, an intensity of light in the specific wavelength range included in the correlation data may be determined on the basis of an intensity detected by the detection device 300 when a predetermined time has elapsed since the start of detection of a virus concentration. The detection starting time of a virus concentration may be the time at which the sample liquid 3061 is dropped on the sensor cell 304. The detection unit 314 may detect the intensity of light in the specific wavelength range when the predetermined time has elapsed since the start of detection of a virus concentration.

The detection device 300 calculates a virus concentration by using a detection value of the detection unit 314 and the correlation data. Alternatively, the calculation of a virus concentration may be performed by another device, such as the controller 400. In this case, the another device includes a memory storing the correlation data.

The detection device 300 is not limited to the above-described example, and another existing method may be used as long as a virus can be detected. Configuration of Controller The controller 400 controls the operation of the entire pathogen detection apparatus 10. Specifically, the controller 400 controls the collection device 200, the detection device 300, and the display device 500. The controller 400 obtains a measurement result of a body temperature measured by the body temperature measurement device 100.

More specifically, the controller 400 controls the start of measurement, causes the suction device 202 to start sucking the surrounding air, and causes the pump 206 to supply a collection liquid from the collection liquid tank 204 to the cyclone 208. Accordingly, the collection liquid is mixed with microparticles in the cyclone 208, and a specimen is supplied from the cyclone 208 to the detection device 300. Furthermore, the controller 400 causes the light source 308 to radiate light and causes the detection unit 314 to detect surface-enhanced fluorescence.

For example, the controller 400 controls the collection device 200 and the detection device 300 in accordance with a body temperature measurement result output by the body temperature measurement device 100. The controller 400 causes the display device 500 to display a detection result obtained by the detection device 300. The controller 400 is capable of controlling each pump to supply a predetermined volume of sample liquid to the detection device 300 under a preset condition on the basis of an input parameter. Furthermore, the controller 400 may have a time measurement function, and may generate and store information on the times taken for individual operations. The controller 400 may receive a measurement value from the detection device 300, and may calculate a chronological change in the concentration of a virus suspended in the air on the basis of the measurement value and time information.

The controller 400 is implemented by, for example, one or more dedicated electronic circuits. The one or more dedicated electronic circuits may be integrated on a single chip or may be individually formed on chips. Alternatively, the controller 400 may be implanted by, instead of the one or more dedicated electronic circuits, a general-purpose processor (not illustrated) and a memory (not illustrated) storing a software program or instruction. In this case, the processor functions as the controller 400 when the software program or instruction is executed.
Configuration of Display Device The display device 500 displays information such as a body temperature measurement result and a virus detection result. The display device 500 is, for example, a liquid crystal display, an organic electroluminescence (EL) display, or electronic paper. The display device 500 is not limited to the above examples, and another existing display device capable of displaying information may be used.

Next, a detection method in the detection device 300 will be described in detail.

One influenza virus contains virus components including about 1000 nucleoprotein (NP) molecules. Thus, to facilitate the detection by using a larger number of NP molecules, a pretreatment of crushing an influenza virus and extracting the NP molecules contained in the influenza virus may be performed in advance, for example, before causing the pathogen to react with an antibody. To crush the influenza virus, the following method is used: a surface-active agent is injected to break a membrane substance that covers the surface of the influenza virus, and the NP molecules therein are extracted. As the surface-active agent used for crush, Tween 20, Triton X, Sarkosyl, and the like are available. Alternatively, a captured virus may be caused to react with an antibody for detection without being crushed.

The pretreatment may include, in addition to the above-described crush, any one of a process of removing foreign substances, a process of concentrating a virus or virus components, and a process of labeling a virus or virus components with a labeling substance used for detection, such as a fluorescent substance or a magnetic substance. The pretreatment is not limited to the above examples, and another process for promoting detection of a pathogen may be performed. The process for promoting detection of a pathogen may be a process for efficiently detecting the quantity of pathogen or a process for accurately detecting the quantity of pathogen.

It is generally known that detection of a biological material is performed by using an antigen-antibody reaction in which an antigen and an antibody are caused to react with each other. Here, the antigen is an influenza virus or NP, which is a component contained in the influenza virus. The antibody reacts specifically with the antigen and binds to the antigen. Hereinafter, a detection method using an antigen-antibody reaction will be described in detail with reference to FIG. 5.

Figure 5:
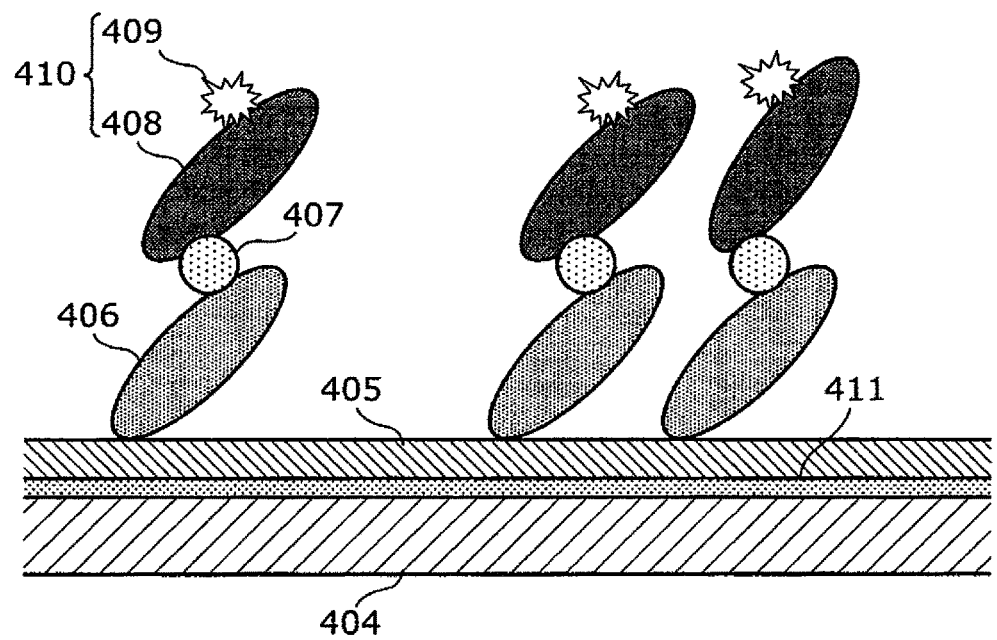
FIG. 5 is a diagram for describing the details of an antigen-antibody reaction.
Figure 6:
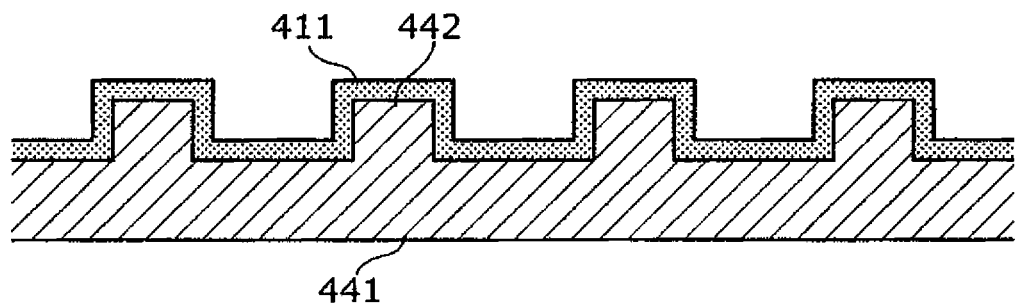
FIG. 6 is a diagram illustrating an example of the structure of a substrate in the case of using surface plasmon resonance.

FIG. 5 is a diagram for describing the details of an antigen-antibody reaction.

First, on a surface of a substrate 404 disposed in the above-described sensor cell 304, first antibodies 406 are formed which bind to a virus or NP as a virus component serving as an antigen. The first antibodies 406 play a role in capturing NP molecules 407 to the vicinity of the surface of the substrate 404. The first antibodies 406 are, for example, IgG antibodies. Among IgG antibodies, those having an ability to bind specifically to an influenza virus or NP as an influenza virus component may be used. The first antibodies 406 are also referred to as capture antibodies. The surface of the substrate 404 is modified with a self-assembled monolayer (SAM) 405 to cause the inorganic substrate and the organic antibodies to bind to each other. The first antibodies 406 are immobilized on the surface of the substrate 404 via the SAM 405.

The SAM 405 is formed on a surface of a gold single-crystal thin layer 411 formed on the surface of the substrate 404. Accordingly, the SAM 405 is a closely-packed and regularly-oriented monolayer formed by the Au—S—R bond resulting from alkanethiol (R—SH) bound to the single-crystal thin layer 411. In this way, in the antigen-antibody reaction, the first antibodies 406 are caused to bind to the SAM 405 formed on the surface of the substrate 404.

Subsequently, a solution containing the NP molecules 407, which are antigens, is injected to the first antibodies 406 immobilized on the surface of the substrate 404. In other words, a solution containing the NP molecules 407 is injected to the detection region 304b of the sensor cell 304. At this time, the first antibodies 406 start binding to the NP molecules 407 as antigens, and then the number of bonds increases as time elapses. While the number of bonds increases, dissociation occurs. Accordingly, the first antibodies 406 and the NP molecules 407 repeat binding and dissociation to reach an equilibrium state.

Subsequently, a solution containing second antibodies 408 is injected to the detection region 304b of the sensor cell 304. Like the first antibodies 406, the second antibodies 408 are, for example, IgG antibodies capable of binding to an influenza virus or the NP molecules 407, which are influenza virus components. A labeling substance 409 that emits a signal for performing detection is bound to each second antibody 408 in advance. The labeling substance 409 may be, for example, a substance that emits fluorescence when being irradiated with laser light having a predetermined wavelength. The labeling substance 409 is, for example, DyLight (registered trademark) 800 that emits fluorescence having a wavelength of 800 nm when being irradiated with laser light having a wavelength of 785 nm. The second antibody 408 to which the labeling substance 409 is bound is also referred to as a labeled antibody 410.

In a case where a virus is present in the air, the virus is captured into the collection liquid 283 in the cyclone 208 when the cyclone 208 is operated. The captured virus is crushed, and thereby the NP molecules 407 in the virus are extracted. As a result of a solution containing the NP molecules 407 obtained accordingly being injected to the detection region 304b of the sensor cell 304, in other words, being injected to the surface of the substrate 404 disposed in the sensor cell 304, the NP molecules 407 bind to the first antibodies 406 serving as capture antibodies formed on the surface of the substrate 404. Furthermore, as a result of injection of a solution containing the second antibodies 408 serving as labeled antibodies each bound to the labeling substance 409 that emits fluorescence, the second antibodies 408 bind to the NP molecules 407, which are antigens bound to the first antibodies 406. The binding between the first antibodies 406, the NP molecules 407 as antigens, and the second antibodies 408 is referred to as sandwich assay. The solution in the detection region 304b in which sandwich assay has occurred is irradiated with laser light, which is excitation light for exciting fluorescence in the labeling substances 409 bound to the second antibodies 408, the excited fluorescence is measured, and accordingly a signal to be detected can be obtained.

The light source 308 repeatedly irradiates the sensor cell 304 with laser light. Accordingly, the detection unit 314 repeatedly detects fluorescence excited from the labeling substances 409. The light source 308 may irradiate the sensor cell 304 with laser light at a predetermined interval. In a case where the sensor cell 304 is repeatedly irradiated with laser light, the intensity of fluorescence that is emitted increases as the number of bonds between the first antibody 406, the NP molecule 407, and the labeled antibody 410 increases. A labeled antibody 410 that does not bind to any NP molecule 407 is suspended in a liquid layer. The number of bonds between the NP molecule 407 and the labeled antibody 410 changes in accordance with the amount of injected solution or the thickness of the liquid layer held in the sensor cell 304.

In an early stage after the solution of the labeled antibodies 410 is injected, the number of bonds between the NP molecule 407 and the labeled antibody 410 gradually increases. When the intensity of laser light that excites fluorescence in the labeling substances 409 of the labeled antibodies 410 is increased, the labeling substance 409 of a suspended labeled antibody 410 that is not bound to any NP molecule 407 emits light. Detecting of the fluorescence emitted at this time does not lead to accurate detection of the NP molecules 407, and thus it is not possible to indiscriminately increase the intensity of laser light. On the other hand, when the quantity of virus in the air is very small, a small quantity of NP molecules 407 is obtained, and thus the intensity of excitation light may be increased in this case.

To increase the strengths of signals from the labeled antibodies 410 bound to the NP molecules 407 near the surface of the substrate 404, surface plasmon resonance is used. FIG. 6 is a diagram illustrating an example of the structure of a substrate in the case of using surface plasmon resonance.

Surface plasmon resonance has traditionally been known. For example, as illustrated in FIG. 6, nano-size protrusions 442 are formed on a surface of a substrate 441, the single-crystal thin layer 411 made of Au or the like is formed on the surfaces of the protrusions 442, and thereby a strong-electromagnetic-field region is formed near the surface of the substrate 441. The strong-electromagnetic-field region is formed very close to the surface of the substrate 441, which enables the labeling substance 409 emitting a signal of the second antibody 408 bound to the NP molecule 407 to emit light whose intensity is higher than that of the light emitted by the labeling substance 409 of the labeled antibody 410 that is suspended away from the surface of the substrate 441 and is not bound to the NP molecule 407. The combination of surface plasmon resonance and sandwich assay makes it possible to effectively detect a very small quantity of virus in the air and to effectively detect a transient state in which the signal strength gradually increases in an early stage after the second antibodies 408 and the NP molecules 407 start binding to each other.

Next, the functional configuration of the pathogen detection apparatus 10 will be described.

Figure 7:
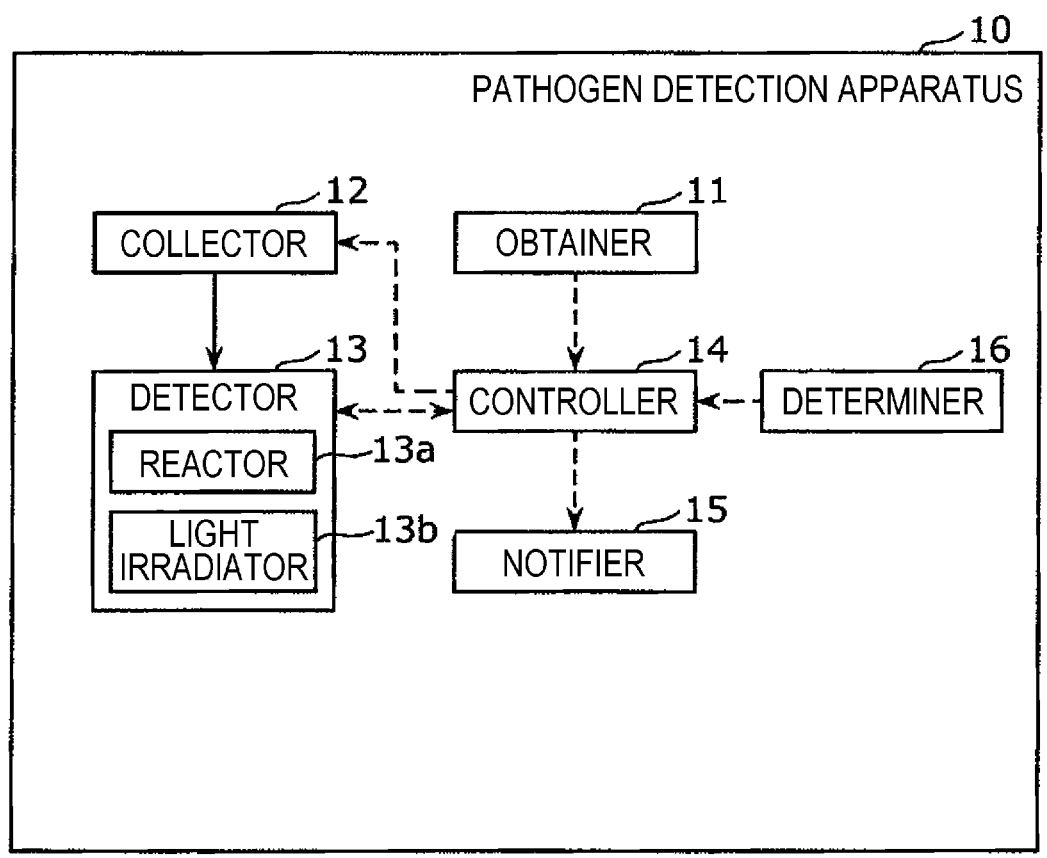
FIG. 7 is a block diagram illustrating an example of the functional configuration of the pathogen detection apparatus according to the embodiment.

FIG. 7 is a block diagram illustrating an example of the functional configuration of the pathogen detection apparatus 10 according to the embodiment.

As illustrated in FIG. 7, the pathogen detection apparatus 10 includes an obtainer 11, a collector 12, a detector 13, a controller 14, a notifier 15, and a determiner 16.

The obtainer 11 obtains a body temperature of a subject. The obtainer 11 obtains a body temperature of a subject by measuring the body temperature of the subject. The obtainer 11 is implemented by, for example, the body temperature measurement device 100. The obtainer 11 may measure a body temperature of a subject and may output information indicating the body temperature.

The collector 12 has a function of performing a pathogen collection operation for collecting a pathogen carried by the subject or a pathogen in air around the subject. The pathogen carried by the subject or the pathogen in air around the subject is, for example, a pathogen contained in breath exhaled by the subject. The pathogen contained in the breath exhaled by the subject is a pathogen carried by the subject before being exhaled by the subject, and is contained in the air around the subject after being exhaled by the subject. The pathogen is a virus, for example, an influenza virus. The collector 12 discharges a specimen, which is obtained by mixing the pathogen into a collection liquid, to the detector 13. The collector 12 is implemented by, for example, the collection device 200. The collector 12 collects air containing breath of the subject. The breath of the subject may contain a pathogen carried by the subject. The air containing the breath of the subject may contain a pathogen contained in the air around the subject.

The detector 13 has a function of performing a pathogen detection operation for detecting the pathogen collected by the collector 12. In a case where a pathogen is not collected by the collector 12, a pathogen as a detection target is absent and thus a detection result obtained by the detector 13 is negative. The detector 13 specifically includes a reactor 13a and a light irradiator 13b.

The reactor 13a causes the pathogen collected by the collector 12 and the labeling substances 409 to react with each other. For example, the reactor 13a causes the first antibodies 406, the NP molecules 407, and the second antibodies 408 to which the labeling substances 409 bound to react with each other, thereby causing them to bind to each other. In this way, the "reaction between a pathogen and a labeling substance" includes an indirect reaction between a pathogen and a labeling substance, that is, a reaction between a pathogen and a substance (antibody) bound to a labeling substance. The reaction in the reactor 13a is not limited to a reaction using surface plasmon resonance, and may be any reaction involving binding between a pathogen and the labeling substances 409. The reactor 13a is implemented by, for example, the sensor cell 304 of the detection device 300.

The light irradiator 13b irradiates, with excitation light, a reacted substance (i.e., a specimen) obtained through the reaction in the reactor 13a. The light irradiator 13b is implemented by, for example, the light source 308.

Accordingly, the detector 13 detects the quantity of pathogen contained in the specimen on the basis of the intensity of fluorescence generated by the labeling substances 409 as a result of irradiation with the excitation light. The detector 13 may detect the intensity of fluorescence generated by the labeling substances 409 as a result of irradiation with the excitation light, and may detect whether or not the subject is infected with a pathogen in accordance with whether or not the detected intensity of fluorescence is higher than a predetermined threshold value. For example, in a case where the detected intensity of fluorescence is higher than the predetermined threshold value, the detector 13 detects that the subject is infected with a pathogen, and obtains a positive detection result. For example, in a case where the detected intensity of fluorescence is lower than or equal to the predetermined threshold value, the detector 13 detects that the subject is not infected with a pathogen, and obtains a negative detection result.

The detector 13 may detect the quantity of labeling substance on the basis of the detected intensity of fluorescence, and correlation data between the intensity of fluorescence and the quantity of labeling substance stored in advance. On the basis of the intensity of fluorescence detected when a predetermined time has elapsed since the start of reaction in the reactor 13a, that is, since the start of detection, and the correlation data, the detector 13 may specify the quantity of labeling substance associated with the detected intensity of fluorescence in the correlation data, and may output the specified quantity of labeling substance. The quantity of labeling substance is correlated with the number of pathogens contained in the specimen or a pathogen concentration in the specimen. Thus, the number of pathogens or a pathogen concentration may be output on the basis of the quantity of labeling substance and the correlation data between the quantity of labeling substance and the number of pathogens or a pathogen concentration stored in advance.

The correlation data may include the correlations between the intensity of fluorescence and the quantity of labeling substance at the elapse of two or more different times.

The detector 13 may perform a pretreatment for promoting detection on the pathogen collected by the collector 12.

The detector 13 is implemented by, for example, the detection device 300, the controller 400, and the like.

The controller 14 controls the detector 13 to perform another pathogen detection operation in a case where the body temperature of the subject obtained by the obtainer 11 is higher than a predetermined threshold value and the detection result obtained by the detector 13 is negative. For example, the controller 14 performs, a predetermined number of times, an operation of controlling the detector 13 to perform another pathogen detection operation. At the time of the another pathogen detection operation, various conditions including a time taken for the detection, a laser used in the detection, and correlation data may be identical to or different from the conditions used in the first detection operation. Before controlling the detector 13 to perform another pathogen detection operation, the controller 14 may control the collector 12 to perform another pathogen collection operation. In this case, the controller 14 controls the detector 13 to perform another pathogen detection operation for detecting the pathogen collected by the collector 12 after completely discharging, by cleaning or the like, the pathogen for which the first pathogen detection operation has been performed. Hereinafter, for example, a description will be given under the assumption that, in a case where the body temperature of the subject obtained by the obtainer 11 is higher than the predetermined threshold value and the detection result obtained by the detector 13 is negative, the controller 14 controls the collector 12 to perform another pathogen collection operation and controls the detector 13 to perform another pathogen detection operation for detecting the pathogen collected by the collector 12. In other words, the controller 14 controls the collector 12 and the detector 13 again in a case where the body temperature of the subject obtained by the obtainer 11 is higher than the predetermined threshold value and the detection result obtained by the detector 13 is negative, and the controller 14 controls neither the collector 12 nor the detector 13 again regardless of whether the detection result obtained by the detector 13 is negative or positive in a case where the body temperature is lower than or equal to the predetermined threshold value.

The controller 14 is implemented by, for example, the controller 400.

The notifier 15 provides a notification indicating the detection result obtained by the detector 13. For example, the notifier 15 may provide a notification indicating a detection result indicating whether or not the subject is infected with a pathogen or a detection result indicating the quantity of labeling substance of a detected pathogen. Although the details will be described below, the notifier 15 may further provide a notification about a pathogen collection method in the collector 12 in a case where the body temperature of the subject obtained by the obtainer 11 is higher than the predetermined threshold value and the detection result obtained in the detector 13 is negative. The notifier 15 is implemented by, for example, the display device 500, and provides the notification by using displaying.

The notifier 15 may provide the notification by using a sound, by producing a printed matter, or by turning on a light source, such as a light emitting diode (LED), instead of using displaying.

The determiner 16 determines, in accordance with a predetermined instruction, whether or not the controller 14 controls the detector 13 to perform another pathogen detection operation. The predetermined instruction is, for example, an instruction from the subject, an instruction based on a predetermined setting about whether or not to perform another pathogen detection operation, or the like. The determiner 16 causes the controller 14 to control the detector 13 not to perform another pathogen detection operation in a case where the predetermined instruction indicates that another pathogen detection operation is not to be performed, and causes the controller 14 to control the detector 13 to perform another pathogen detection operation in a case where the predetermined instruction indicates that another pathogen detection operation is to be performed.

The determiner 16 is implemented by, for example, the controller 400.

Relationship between Quantity of Carried Virus and Body Temperature

Next, the relationship between the quantity of virus carried by a subject and the body temperature of the subject will be described with reference to FIG. 8.

Figure 8:
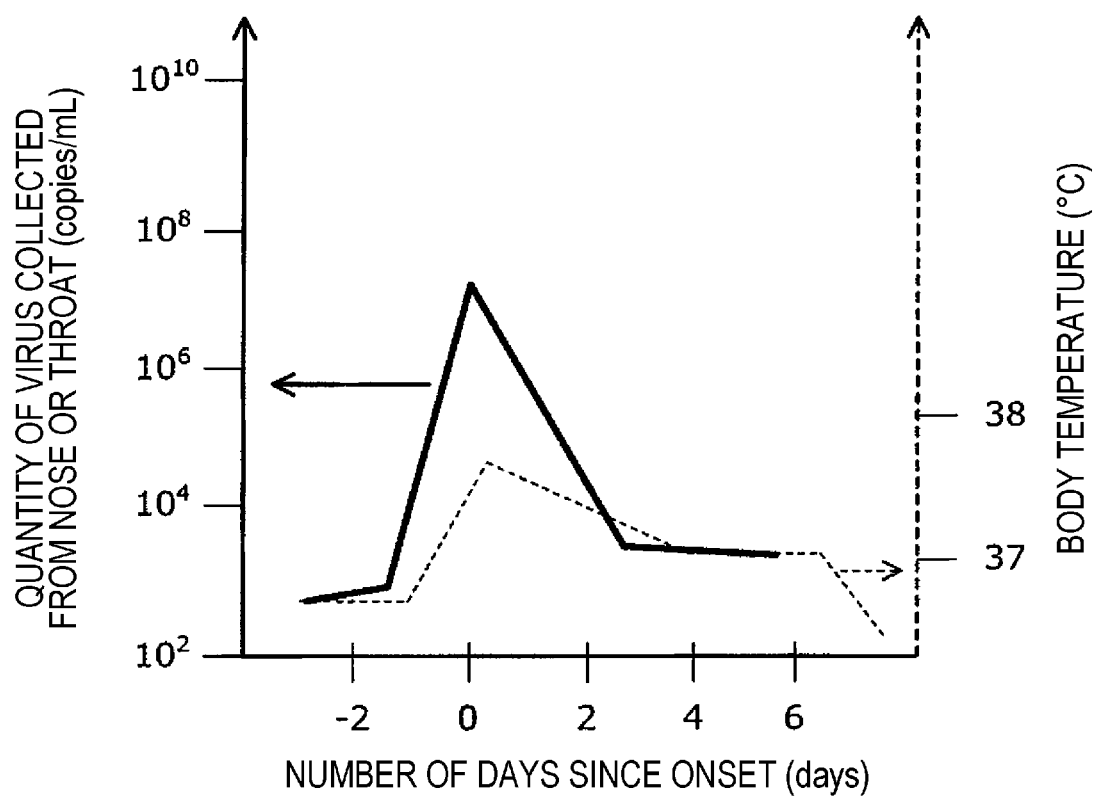
FIG. 8 is a graph illustrating a relationship between the quantity of virus carried by a subject and a body temperature of the subject.

FIG. 8 is a graph illustrating the relationship between the quantity of virus carried by a subject and the body temperature of the subject. In FIG. 8, the vertical axis on the left represents the quantity of virus collected from the nose or throat of the subject, the vertical axis on the right represents the body temperature of the subject, and the horizontal axis represents the number of days since onset, that is, since when a symptom caused by the virus appears. The day of onset is represented by 0.

It is understood from FIG. 8 that there is a positive correlation between the quantity of virus and the body temperature. Accordingly, it can be estimated that, in a case where the body temperature of the subject is higher than the predetermined threshold value, there is a high possibility that the subject carries the virus in high concentration. The predetermined threshold value is a body temperature higher than a normal body temperature of the subject and may be, for example, 37° C. The predetermined threshold value may vary among subjects and may be, for example, a value obtained by adding 1° C. to a normal body temperature. That is, when the normal body temperature of a subject is 36° C., 37° C. may be set as the predetermined threshold value, and when the normal body temperature of a subject is 36.5° C., 37.5° C. may be set as the predetermined threshold value.

Operation of Pathogen Detection Apparatus

Next, an operation of the pathogen detection apparatus 10 will be described.

Figure 9:
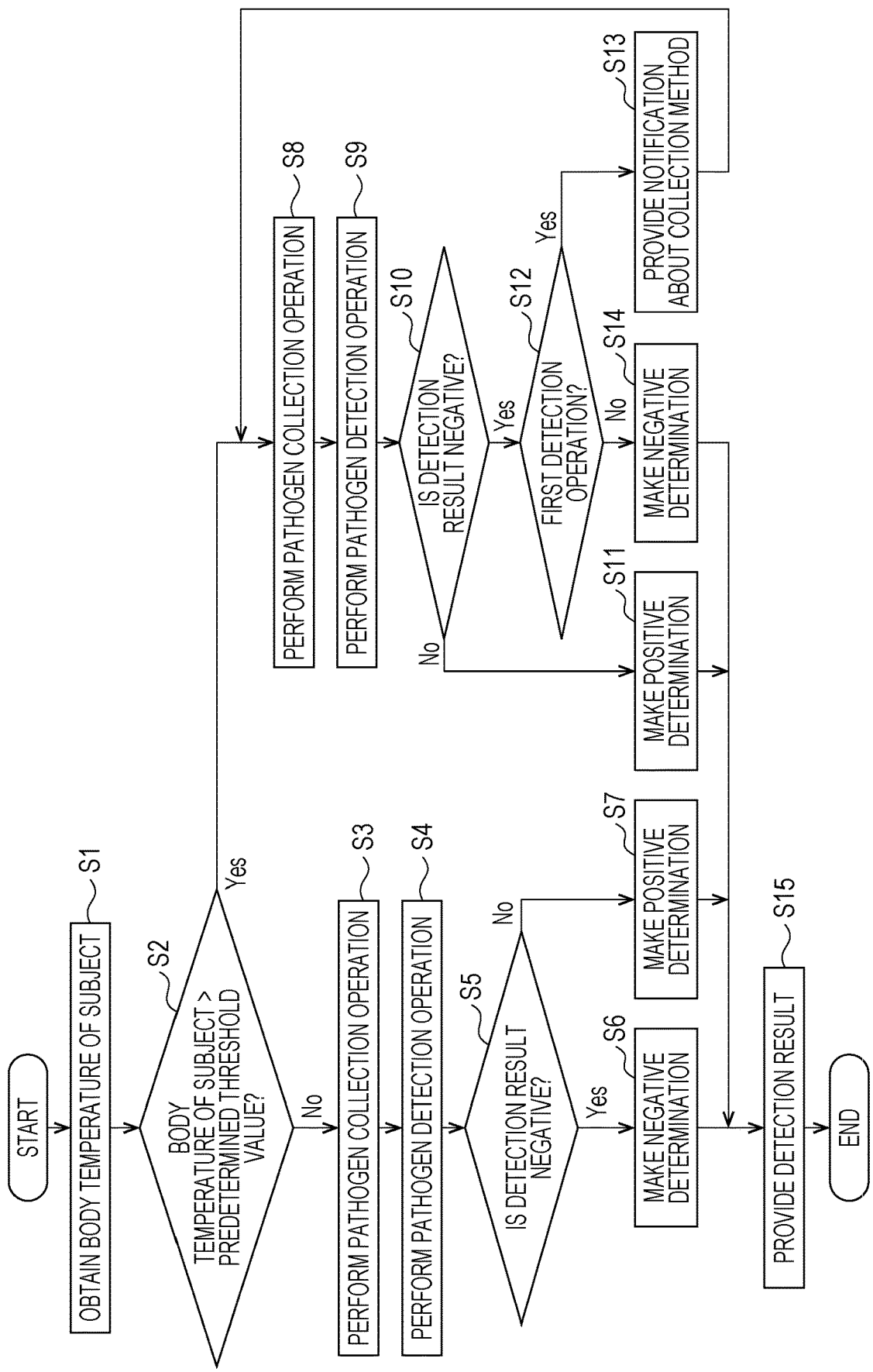
FIG. 9 is a flowchart illustrating an example of the operation of the pathogen detection apparatus according to the embodiment.

FIG. 9 is a flowchart illustrating an example of the operation of the pathogen detection apparatus 10 according to the embodiment.

First, the obtainer 11 obtains a body temperature of a subject (S1).

Subsequently, the controller 14 determines whether or not the body temperature obtained by the obtainer 11 is higher than a predetermined threshold value (S2).

In a case where it is determined that the body temperature of the subject obtained by the obtainer 11 is lower than or equal to the predetermined threshold value (NO in S2), the collector 12 performs a pathogen collection operation for collecting a pathogen carried by the subject or a pathogen in air around the subject (S3). For example, the collector 12 collects breath of the subject and sends the collected specimen to the detector 13.

Subsequently, the detector 13 preforms a pathogen detection operation for detecting the pathogen collected by the collector 12 (S4). For example, the detector 13 causes the pathogen collected by the collector 12 to react with the labeling substances 409 and irradiates a reacted substance with excitation light.

Subsequently, the controller 14 determines whether or not a detection result obtained by the detector 13 is negative (S5). For example, in a case where a detected intensity of fluorescence is higher than a predetermined threshold value, the detector 13 detects that the subject is infected with a pathogen and obtains a positive detection result. For example, in a case where a detected intensity of fluorescence is lower than or equal to the predetermined threshold value, the detector 13 detects that the subject is not infected with a pathogen and obtains a negative detection result.

In a case where the detection result is negative (YES in S5), the controller 14 makes a negative determination without performing a pathogen detection operation and so forth any more (S6).

In a case where the detection result is positive (NO in S5), the controller 14 makes a positive determination (S7).

In this way, in a case where the body temperature of the subject is lower than or equal to the predetermined threshold value, a pathogen detection operation and so forth are not performed any more, and a notification indicating the detection result obtained by the detector 13 is provided. This is because, in a case where the body temperature of the subject is low, the possibility that the subject is infected with a pathogen is low and the necessity for another pathogen detection operation is low.

On the other hand, in a case where it is determined that the body temperature of the subject obtained by the obtainer 11 is higher than the predetermined threshold value (YES in S2), the collector 12 performs a pathogen collection operation for collecting a pathogen carried by the subject or a pathogen in air around the subject as in the case where the body temperature of the subject is lower than or equal to the predetermined threshold value (S8), the detector 13 performs a pathogen detection operation for detecting the pathogen collected by the collector 12 (S9), and the controller 14 determines whether or not a detection result obtained by the detector 13 is negative (S10).

In a case where the detection result is positive (NO in S10), the controller 14 makes a positive determination (S11).

In a case where the detection result is negative (YES in S10), the controller 14 determines whether the pathogen detection operation performed for the subject by the detector 13 is the first pathogen detection operation (S12). The first pathogen detection operation herein means, for example, the first pathogen detection operation during a latest period of several minutes to several tens of minutes, and does not mean that this is the first time to perform a pathogen detection operation for the subject by using the pathogen detection apparatus 10.

In a case where the pathogen detection operation performed by the detector 13 is the first pathogen detection operation (YES in S12), the notifier 15 provides a notification about a pathogen collection method in the collector 12 (S13). Now, a notification about a pathogen collection method in the collector 12 will be described with reference to FIG. 10.

Figure 10:
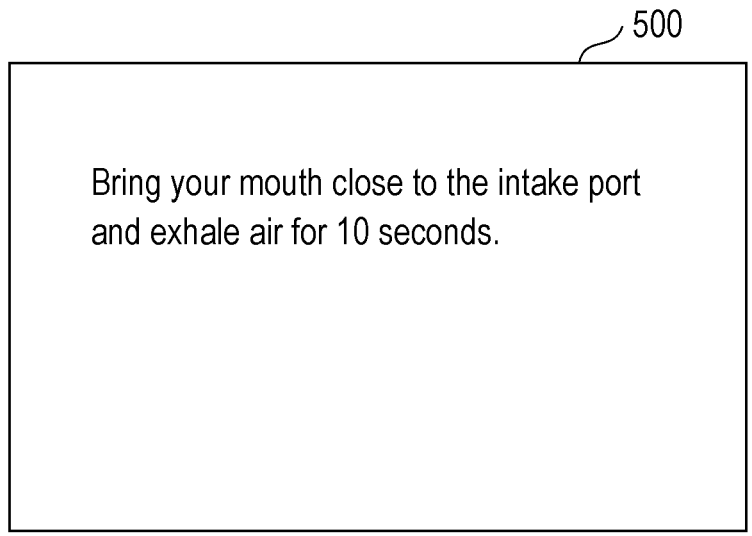
FIG. 10 is a diagram illustrating an example of a notification about a collection method provided by a notifier according to the embodiment.

FIG. 10 is a diagram illustrating an example of a notification about a collection method provided by the notifier 15 according to the embodiment. FIG. 10 illustrates the display device 500 serving as the notifier 15, and also illustrates a notification about a collection method displayed on the display device 500.

For example, there is a possibility that breath collection was not correctly performed, and thus an instruction prompting the subject to correctly perform breath collection is displayed for the subject, as illustrated in FIG. 10. Specifically, the subject is prompted to bring his/her mouth close to the air intake port 210 so that leakage of breath from the air intake port 210 is minimized, and is also prompted to exhale air for a long time, for example, ten seconds, so that a larger amount of pathogen is collected. This increases a possibility that an accurate detection result is obtained in the following pathogen detection operation, which will be described below.

Although this subject has a high body temperature and the possibility of being infected with a pathogen is high, the detection result of the first pathogen detection operation was negative, that is, no pathogen was detected in the first pathogen detection operation. Thus, there is a possibility that an error occurred in the detection, for example, breath collection was not correctly performed or an antigen-antibody reaction was not correctly performed. In other words, if a negative determination is made, that may be a false negative. Thus, the process from step S8 is performed again. Specifically, the controller 14 controls the collector 12 to perform another pathogen collection operation for collecting a pathogen (S8 is performed again), and controls the detector 13 to perform another pathogen detection operation for detecting the pathogen collected by the collector 12 (S9 is performed again).

When controlling the collector 12 to perform the another pathogen collection operation, the controller 14 may perform control so that a time taken for the another pathogen collection operation is longer than a time taken for the preceding pathogen collection operation. This is because, when the time taken for the another pathogen collection operation is longer, a larger amount of pathogen may be collected. For example, the time taken for the another pathogen collection operation may be twice or more the time taken for the preceding pathogen collection operation. For example, the controller 14 may increase the time during which air is taken into the cyclone 208 from the air intake port 210, or may increase the time taken for the process in the cyclone 208.

When controlling the detector 13 to perform the another pathogen detection operation, the controller 14 may perform control so that a time taken for the another pathogen detection operation is longer than a time taken for the preceding pathogen detection operation. For example, the time taken for the another pathogen detection operation may be twice or more the time taken for the preceding pathogen detection operation. This is because, in a case where the number of bonds between the labeled antibody 410, the NP molecule 407, and the first antibody 406 is not saturated during the time of the preceding pathogen detection operation, an increase in the number of bonds can be expected during the time of the another pathogen detection operation.

For example, the controller 14 may control the collector 12 and the detector 13 so that five minutes are taken for collection and detection in the second operation, compared to the first operation in which one minute is taken for collection and detection. In this way, as a result of increasing the time taken for the second collection and detection relative to the time taken for the first collection and detection, an accurate detection result is more likely to be obtained in the second pathogen detection operation.

For example, another pathogen detection operation may be performed by using a detection method different from the method used in the preceding pathogen detection operation. For example, the another pathogen detection operation may be performed by using a detection method that uses antibodies different from the antibodies used in the preceding pathogen detection operation.

In a case where the detection result of the another pathogen detection operation is negative and the pathogen detection operation in the detector 13 is not the first pathogen detection operation (NO in S12), in other words, in a case where another pathogen detection operation has been performed once, the controller 14 makes a negative determination (S14). This is because the detection result of the another pathogen detection operation is also negative, and thus there is an increased possibility of not being a false negative.

Subsequently, the notifier 15 provides a notification indicating the detection result (S15). For example, information indicating a negative or positive result is displayed on the display device 500, and the subject can check whether he/she is negative or positive.

In a case where the body temperature of the subject is higher than the predetermined threshold value and the detection result is negative, the subject may be allowed to determine whether or not another pathogen detection operation is to be performed. This will be described with reference to FIG. 11.

Figure 11:
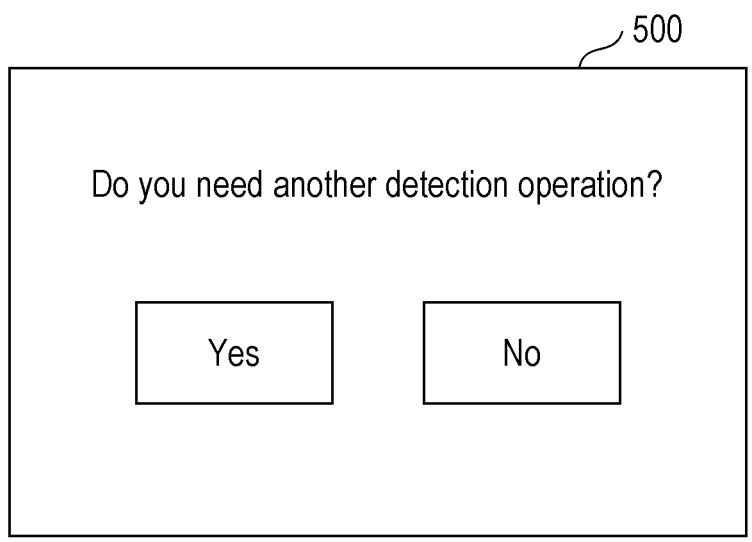
FIG. 11 is a diagram illustrating an example of a notification for allowing a subject to select whether or not another pathogen detection operation is to be performed, provided by the notifier according to the embodiment.

FIG. 11 is a diagram illustrating an example of a notification for allowing the subject to select whether or not another pathogen detection operation is to be performed, provided by the notifier 15 according to the embodiment. FIG. 11 illustrates the display device 500 serving as the notifier 15 and illustrates a notification for allowing the subject to select whether or not another pathogen detection operation is to be performed, displayed on the display device 500.

For example, the subject selects "Yes" displayed on the display device 500 (for example, a touch panel display or the like) in a case where another pathogen detection operation is necessary, and selects "No" in a case where another pathogen detection operation is not necessary. For example, in a case where "Yes" is selected, an instruction (signal) to perform another pathogen detection operation is generated as a predetermined instruction, and the determiner 16 determines, in accordance with the predetermined instruction, that the controller 14 controls the detector 13 to perform another pathogen detection operation. Accordingly, the process including step S13, step S8, and the subsequent steps is performed again. For example, in a case where "No" is selected, an instruction (signal) not to perform another pathogen detection operation is generated as a predetermined instruction, and the determiner 16 determines, in accordance with the predetermined instruction, that the controller 14 does not control the detector 13 to perform another pathogen detection operation. Accordingly, the process including step S13, step S8, and the subsequent steps is not performed again.

In a case where the body temperature of the subject is higher than the predetermined threshold value and the detection result is negative, whether or not to enable the function of performing another pathogen detection operation may be selected by a setting performed by a manager or the like of the pathogen detection apparatus 10. For example, in a case where the setting indicates that another pathogen detection operation is not to be performed, the process including steps S3 to S7 and step S15 may be performed, and the process including step S1, step S2, and steps S8 to S14 is not performed. For example, in a case where the setting indicates that another pathogen detection operation is not to be performed, an instruction (signal) indicating turning off of the function of performing another pathogen detection operation is generated as a predetermined instruction, and the determiner 16 determines, in accordance with the predetermined instruction, that the controller 14 does not control the detector 13 to perform another pathogen detection operation. Accordingly, even if the body temperature of the subject is higher than the predetermined threshold value and the first detection result is negative, another pathogen detection operation is not performed and a negative determination is made.

In the example illustrated in FIG. 9, in a case where the body temperature of the subject obtained by the obtainer 11 is higher than the predetermined threshold value and the detection result obtained by the detector 13 is negative, the controller 14 performs an operation of controlling the detector 13 to perform another pathogen detection operation a predetermined number of times, that is, once, but the predetermined number is not limited thereto. The predetermined number is not limited to one and may be two or more. For example, the predetermined number may be determined to be a certain number by a manager or the like of the pathogen detection apparatus 10.

Advantages and the Like

As described above, the pathogen detection apparatus 10 includes the obtainer 11 that measures a body temperature of a subject and outputs information indicating the body temperature, the collector 12 that performs a pathogen collection operation for collecting a pathogen carried by the subject or a pathogen in air around the subject, the detector 13 that performs a pathogen detection operation for detecting the pathogen collected by the collector 12, the notifier 15 that provides a notification indicating a detection result obtained by the detector 13, and the controller 14. In a case where the body temperature output by the obtainer 11 is higher than a predetermined threshold value and the detection result obtained by the detector 13 is negative, the controller 14 controls the detector 13 to perform another pathogen detection operation for detecting a pathogen.

Accordingly, whether the possibility of being infected with a pathogen is determined on the basis of whether the body temperature of the subject is higher than the predetermined threshold value. In a case where the body temperature of the subject is higher than the predetermined threshold value, another pathogen detection operation is performed even if the detection result is negative. Thus, in a case where the body temperature of the subject is higher than the predetermined threshold value, another pathogen detection operation is performed even if the detection result is negative because of a detection error that occurs in a process in which the pathogen detection apparatus 10 collects a specimen from the subject and performs detection. Thus, false negatives in pathogen detection from subjects can be reduced, and the spread of infection with a pathogen can be prevented.

When controlling the detector 13 to perform the another pathogen detection operation, the controller 14 may perform control so that a time taken for the another pathogen detection operation is longer than a time taken for a preceding pathogen detection operation.

Accordingly, the detection accuracy can be increased as the time taken for pathogen detection is increased. This increases a possibility that an accurate detection result can be obtained in the another pathogen detection operation.

The controller 14 may control the collector 12 to perform another pathogen collection operation for collecting a pathogen before controlling the detector 13 to perform the another pathogen detection operation, and then may control the detector 13 to perform the another pathogen detection operation for detecting the pathogen collected by the collector 12 in the another pathogen collection operation.

Accordingly, because there is a possibility that the cause of a negative detection result in the preceding detection is incorrect collection by the collector 12 of a pathogen to be detected by the detector 13, the possibility of obtaining an accurate detection result in the another pathogen detection operation is increased by performing the another pathogen collection operation.

When controlling the collector 12 to perform the another pathogen collection operation, the controller 14 may perform control so that a time taken for the another pathogen collection operation is longer than a time taken for a preceding pathogen collection operation.

Accordingly, more pathogens can be collected as the time taken for pathogen collection is increased. This increases a possibility that an accurate detection result can be obtained in the another pathogen detection operation.

The pathogen detection apparatus 10 may further include the determiner 16 that determines, in accordance with a predetermined instruction, whether or not the controller 14 controls the detector 13 to perform the another pathogen detection operation.

Accordingly, because another pathogen detection operation is not necessarily desired depending on a situation, whether or not to perform another pathogen detection operation can be determined in accordance with the predetermined instruction.

In a case where the body temperature output by the obtainer 11 is higher than the predetermined threshold value and the detection result obtained by the detector 13 is negative, the controller 14 may perform, a predetermined number of times, an operation of controlling the detector 13 to perform the another pathogen detection operation.

In a case where the body temperature output by the obtainer 11 is higher than the predetermined threshold value and the detection result obtained by the detector 13 is negative, the notifier 15 may provide a notification about a pathogen collection method in the collector 12.

Accordingly, because there is a possibility that the cause of a negative detection result in the preceding detection is incorrect collection by the collector 12 of a pathogen to be detected by the detector 13, it is possible to allow the subject to recognize a correct collection method by providing a notification about the collection method (for example, a notification about the correct collection method).

Other Embodiments

A pathogen detection apparatus according to one or more aspects of the present disclosure has been described above on the basis of an embodiment. The present disclosure is not limited to the embodiment. An embodiment implemented by applying various modifications conceived of by a person skilled in the art to the embodiment, or an embodiment constructed by combining elements in different embodiments, may be included in one or more aspects of the present disclosure without deviating from the gist of the present disclosure.

For example, in the above-described embodiment, the controller 14 performs, when controlling the detector 13 to perform another pathogen detection operation, control so that a time taken for the another pathogen detection operation is longer than a time taken for a preceding pathogen detection operation, but the embodiment is not limited thereto. For example, the time taken for the another pathogen detection operation may be the same as the time taken for the preceding pathogen detection operation.

For example, in the above-described embodiment, the controller 14 performs, when controlling the collector 12 to perform another pathogen collection operation, control so that a time taken for the another pathogen collection operation is longer than a time taken for a preceding pathogen collection operation, but the embodiment is not limited thereto. For example, the time taken for the another pathogen collection operation may be the same as the time taken for the preceding pathogen collection operation.

For example, in the above-described embodiment, the controller 14 controls the collector 12 to perform another pathogen collection operation for collecting a pathogen before controlling the detector 13 to perform another pathogen detection operation, and then controls the detector 13 to perform another pathogen detection operation for detecting the pathogen collected by the collector 12, but the embodiment is not limited thereto. For example, in a case where the body temperature of the subject obtained by the obtainer 11 is higher than the predetermined threshold value and the detection result obtained by the detector 13 is negative, another pathogen collection operation need not necessarily be performed, and another pathogen detection operation may be performed by using the pathogen collected by the collector 12 in the preceding pathogen collection operation.

For example, although the pathogen detection apparatus 10 includes the determiner 16 in the above-described embodiment, the pathogen detection apparatus 10 need not necessarily include the determiner 16.

For example, although the notifier 15 provides a notification about a pathogen collection method in the collector 12 in the above-described embodiment, the notifier 15 need not necessarily provide the notification.

For example, the present disclosure can be implemented as a pathogen detection method executed by the pathogen detection apparatus 10, as well as being implemented as the pathogen detection apparatus 10.

The pathogen detection method is a pathogen detection method for the pathogen detection apparatus 10 including the obtainer 11 that obtains a body temperature of a subject, the collector 12 that performs a pathogen collection operation for collecting a pathogen carried by the subject or a pathogen in air around the subject, the detector 13 that performs a pathogen detection operation for detecting the pathogen collected by the collector 12, the notifier 15 that provides a notification indicating a detection result obtained by the detector 13, and the controller 14. As illustrated in FIG. 9, in a case where the body temperature of the subject obtained by the obtainer 11 is higher than a predetermined threshold value (YES in S2) and the detection result obtained by the detector 13 is negative (YES in S10), the controller 14 controls the detector 13 to perform another pathogen detection operation for detecting a pathogen (S9 is performed again).

A pathogen detection method includes obtaining information indicating a body temperature of a subject, performing first collection for collecting first air containing first breath of the subject, performing first detection for detecting a quantity of pathogen from the first air, performing first determination for determining, based on the first detection, whether the subject is negative, and in a case where the information indicates that the body temperature is higher than a predetermined threshold value and a result of the first determination is negative, performing (a) an i-th process where i is 2 to n, n being an integer that is 2 or greater, or (b) additional detection for detecting a quantity of pathogen from the first air. The i-th process may include i-th collection for collecting i-th air containing i-th breath of the subject, i-th detection for detecting a quantity of pathogen from the i-th air, and i-th determination for determining, based on the i-th detection, whether the subject is negative.

The present disclosure can be implemented as a program for causing a computer to execute the steps included in the pathogen detection method. Furthermore, the present disclosure can be implemented as a non-transitory computer-readable recording medium, such as a CD-ROM, having the program recorded thereon.

For example, in a case where the present disclosure is implemented by a program (software), the individual steps are executed as a result of the program being executed by using hardware resources of the computer, such as a CPU, a memory, and an input/output circuit. In other words, the individual steps are executed as a result of data being obtained from the memory, the input/output circuit, or the like and computed by the CPU, and a computation result being output to the memory, the input/output circuit, or the like by the CPU.

In the above-described embodiment, the individual elements included in the pathogen detection apparatus 10 may be constituted by dedicated hardware or may be implemented as a result of a software program suitable for the individual elements being executed. The individual elements may be implemented as a result of the software program recorded on a recording medium, such as a hard disk or a semiconductor memory, being read out and executed by a program execution unit, such as a CPU or a processor.

Some or all of the functions of the pathogen detection apparatus 10 according to the above-described embodiment are typically implemented as a large scale integration (LSI) circuit, which is an integrated circuit. These functions may be each individually formed as a single chip, or may be integrated into a single chip so as to include some or all of the functions. The circuit integration is not necessarily implemented by the LSI, and may be implemented by a dedicated circuit or a general-purpose processor. A field programmable gate array (FPGA), which is programmable after fabrication of the LSI, or a reconfigurable processor, in which the connections and settings of a circuit cell in the LSI are reconfigurable, may be used.

Some or all of the functions of the pathogen detection apparatus 10 according to the above-described embodiment may be implemented as a result of a program being executed by a processor, such as a CPU.

Some or all of the functions of the pathogen detection apparatus 10 according to the above-described embodiment may be implemented as a result of being executed by an external server.

The numerals used above are merely examples for specifically describing the present disclosure, and the present disclosure is not limited to these numerals.

Various modification examples implemented by applying changes conceived of by a person skilled in the art to the embodiment of the present disclosure are also included in the present disclosure without deviating from the gist of the present disclosure.

The present disclosure is useful as a pathogen detection apparatus, a pathogen detection method, and the like that are capable of detecting a pathogen from a subject or a space around the subject.

What is claimed is:

1. A pathogen detection apparatus comprising:
a temperature sensor configured to measure a body temperature of a subject and output information indicating the body temperature;
a collector, including at least one pump, a suction device, a cyclone element, at least one liquid tank, and a liquid channel, configured to perform a first pathogen collection operation for collecting at a first time period a first pathogen sample carried by the subject or included in air around the subject during the first time period;
a detector, including at least a reactor and light irradiator, configured to perform a first pathogen detection operation for detecting a first pathogen in the first pathogen sample collected by the collector;

a user interface configured to provide a first notification indicating to the subject a detection result obtained by the detector; and a controller, wherein in a case where the body temperature output by the temperature sensor is higher than a predetermined threshold value and the detection result obtained by the detector is negative, the controller is configured to control the collector to perform a second pathogen collection operation for collecting at a second time period a second pathogen sample carried by the subject or included in the air around the subject during the second time period and configured to cause the detector to perform a second pathogen detection operation for detecting a second pathogen in the second pathogen sample, and wherein the first time period is different than the second time period.

2. The pathogen detection apparatus according to claim 1, wherein when controlling the detector to perform the second pathogen detection operation, the controller is configured to control the detector so that a time taken for the second pathogen detection operation is longer than a time taken for the first pathogen detection operation.

3. The pathogen detection apparatus according to claim 1, wherein the controller is configured to control the collector to perform the second pathogen collection operation for collecting the second pathogen before controlling the detector to perform the second pathogen detection operation, and configured to control the detector to perform the second pathogen detection operation for detecting the second pathogen collected by the collector in the second pathogen collection operation.

4. The pathogen detection apparatus according to claim 3, wherein when controlling the collector to perform the second pathogen collection operation, the controller is configured to control the collector so that a time taken for the second pathogen collection operation is longer than a time taken for the first pathogen collection operation.

5. The pathogen detection apparatus according to claim 1, wherein the controller is further configured to determine, in accordance with a predetermined instruction, whether or not to control the detector to perform the second pathogen detection operation.

6. The pathogen detection apparatus according to claim 1, wherein in a case where the body temperature output by the temperature sensor is higher than the predetermined threshold value and the detection result obtained by the detector is negative, the controller is configured to perform, a predetermined number of times, an operation of controlling the detector to perform a pathogen detection operation.

7. The pathogen detection apparatus according to claim 1, further comprising:

an intake port, wherein the collector is configured to collect the first pathogen sample and the second pathogen sample through the intake port, in a case where the body temperature output by the temperature sensor is higher than the predetermined threshold value and the detection result obtained by the detector is negative, the user interface is configured to provide a second notification about a pathogen collection method in the collector, the second notification includes a notification prompting the subject to bring the subject's mouth close to the air intake port so that leakage of breath from the air intake port is minimized.

8. A pathogen detection method comprising:

obtaining information indicating a body temperature of a subject and outputting information indicating the body temperature;

performing a first pathogen collection for collecting at a first time period a first air sample containing a first breath of the subject;

performing a first detection for detecting a quantity of a first pathogen in the first air sample;

performing a first determination for determining, based on the first detection, whether the subject is negative; and in a case where the information indicates that the body temperature is higher than a predetermined threshold value and a result of the first determination is negative, performing a second pathogen collection for collecting at a second time period a second air sample containing a second breath of the subject and performing a second detection for detecting a quantity of a second pathogen in the second air sample, wherein the first time period is different than the second time period.

9. The pathogen detection method according to claim 8, wherein in a case where the information indicates that the body temperature is higher than the predetermined threshold value and the result of the first determination is negative, the pathogen detection method further comprises providing a notification about a pathogen collection method, wherein the notification includes a notification prompting the subject to bring the subject's mouth close to an air intake port so that leakage of breath from the air intake port is minimized.

\* \* \* \* \*